US00PP34224P2

(12) United States Plant Patent
Hansen

(10) Patent No.: US PP34,224 P2
(45) Date of Patent: May 10, 2022

(54) ***HOSTA* PLANT NAMED 'LOVE STORY'**

(50) Latin Name: ***Hosta* hybrid (Tratt.)**
Varietal Denomination: Love Story

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,987

(22) Filed: Jan. 10, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12; A01H 5/02
See application file for complete search history.

*Primary Examiner* — Keith O. Robinson

(57) ABSTRACT

A new and distinct *Hosta* plant named 'Love Story' producing medium-sized low mounds of basal, broadly lanceolate, leaves with long narrowly acute apices, cordate bases and slightly wavy margins. The leaves are variegated having dark green margins and pale-yellow centers with intermediate color separation between the margin and center of variably large segments of several shades of chartreuse. The medium-sized leaves have a matte upper surface and glaucous underside. The campanulate flowers are pale lavender with white edges appearing beginning in mid-June. Each flower is attractively subtended by a floral bract that mimic the leaf variegation making the scape showy for long periods. 'Love Story' is useful in the landscape, as a container plant, a specimen or en masse.

2 Drawing Sheets

Botanical classification: *Hosta* hybrid (Tratt.).
Variety denomination: 'Love Story'.

STATEMENT REGARDING PRIOR DISCLOSURES UNDER 37 CFR 1.77(B)(6)

*Hosta* 'Love Story' was first introduced by the inventor as a non-enabling description in registration of the name in early 2021 with the International Cultivar Registration Authority for the genus *Hosta*. No plants of *Hosta* 'Love Story' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Love Story' hereinafter also referred to as the new plant or by the cultivar name, 'Love Story'. *Hosta* 'Love Story' was hybridized by the inventor on Jul. 13, 2015 at a wholesale perennial nursery in Zeeland, Mich., USA. The female parent was the proprietary unreleased streaked sport of 'Niagara Falls' (not patented) and the male parent was 'Viking Ship' (not patented). The seeds from this cross were planted in late fall of 2015 and a single seedling selection from this cross eventually produced the new plant. The new plant was assigned the breeder code 15-24-1 and passed the initial evaluation in the summer of 2018. 'Love Story' has been asexually propagated by division at the same nursery since 2018 and also by careful shoot tip plant tissue culture with the resultant asexually propagated plants having retained all the same traits as the original plant. *Hosta* 'Love Story' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Angel Falls' U.S. Plant Pat. No. 28,785, 'American Sweetheart' (not patented), 'Sea Thunder' (not patented), 'Lakeside Paisley Print' (not patented), 'Cool As a Cucumber' (not patented), 'Lakeside Love Affair' (not patented), 'Half and Half' (not patented), 'Miss America' U.S. Plant Pat. No. 32,068, and 'Viva Las Vegas' (not patented).

The female parent is larger and more arching in habit and larger in foliage size, the variegation is thinly spread out in sectors throughout the leaves rather than with the lighter sector all being confined to the middle of the leaves, and the scape is more green. The male parent 'Viking Ship' is larger habit with more rounded and solid bluish-green colored foliage with less sinuate margins, and the scapes are shorter and bluish-green colored.

The habit of 'Angel Falls' is smaller and more arching in habit with a more greenish-yellow leaf center earlier in the season and slightly more vein pairs and the flowers are more flared. 'American Sweetheart' has thicker and stiffer foliage and more upright habit, and the leaves have a wider margin and narrower center with less intermediate variegated colors between the margin and center. 'Sea Thunder' has smaller habit and smaller foliage with less intermediate colors between the margin and center, and the flowers are more pigmented medium lavender. 'Lakeside Paisley Print' has a stiffer and thicker substance foliage with broader margins and narrower center variegation, the scapes become more lavender blushed, and the flowers are darker purple. 'Cool As a Cucumber' has a longer more lanceolate and arching foliage. 'Lakeside Love Affair' has foliage that is more broadly ovate with less intermediate colors between the margin and center variegation. 'Half and Half' has smaller, heavier-substance, smaller and thicker leaves on a plant with a shorter habit. 'Miss America' has stiffer and thicker foliage with broader margins and narrower variegated leaf center, and the flowers are larger, open wider and have a darker lavender center stripe. 'Viva Las Vegas' has foliage that is broader, more cordate and more bullate and less sinuate and the margin color is more bluish-green.

Other *Hosta* cultivars may have individual traits similar to 'Love Story' but the new plant differs from the above listed cultivars and all other *Hostas* known to the applicant, by the combination of the following traits.

1. Leaves are medium-sized, broadly lanceolate, with long, narrowly, acute apices and cordate bases;
2. Leaves have a slightly wavy margin and have slightly impressed adaxial veins;
3. Leaf margins are dark green, the mature center color is pale yellow with intermediate color separation between the margin and center of variably large segments of several shades of chartreuse;
4. Campanulate flowers are pale lavender on upright, creamy-colored scapes with light blush of lavender beginning in mid-June;
5. Flowers are densely arranged on scapes with the first flowers beginning to open well above the foliage;
6. Floral bracts have a variegation that mimics the foliage subtend each flower;
7. The habit is a medium-sized low mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show a five-year-old 'Love Story' plant in a trial garden at a nursery in Zeeland, Mich. with supplement fertilizer and water as needed.

DETAILED BOTANICAL DESCRIPTION

Figure 1:
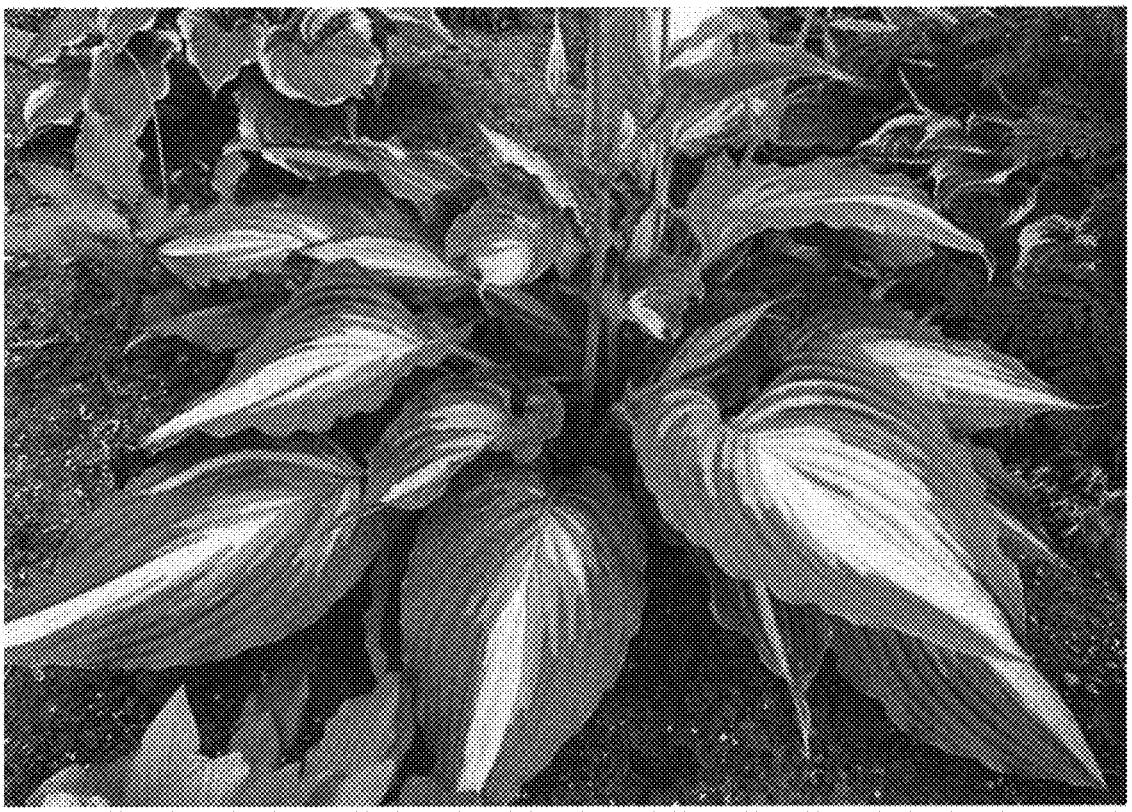
FIG. 1 shows the landscape foliage habit of a new plant prior to flowering.
Figure 2:
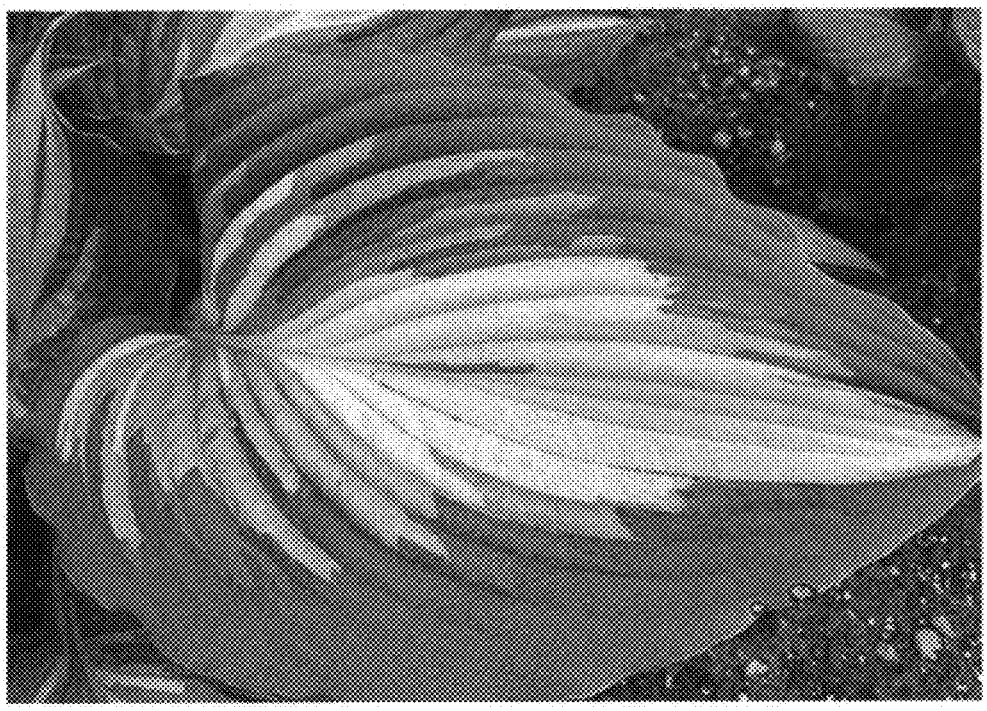
FIG. 2 shows a close-up of a leaf.
Figure 3:
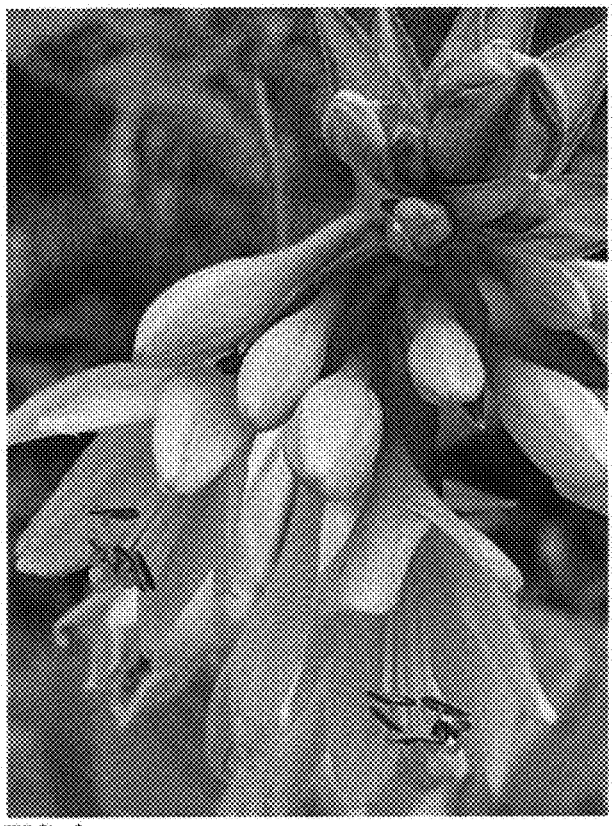
FIG. 3 shows a close-up of the flower, buds and foliar bracts.

The following descriptions and color references are based on the 2015 edition of The Royal Horticultural Society Colour Chart except where common dictionary terms are used. The new plant, *Hosta* 'Love Story', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a five-year-old plant in a shaded trial garden in Zeeland, Mich. with supplemental water and fertilizer.

Botanical classification: *Hosta* x hybrid;

Parentage: Female or seed parent is a proprietary sport of 'Niagara Falls'; male or pollen parent is 'Viking Ship';

Propagation: Garden division and sterile shoot tip tissue culture;

Time to initiate roots from tissue culture: About three weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a low medium-sized mound of outwardly extending petioles and leaves and arching scapes flowering above foliage;

Plant size: Foliage height to about 35.6 cm above soil line to the top of the leaves, to about 68.5 cm tall to the top of the flowers and to about 78.7 cm wide at the widest point just above the soil line;

Foliage description: Broadly lanceolate; narrowly acute apex, cordate base; margin entire, and slightly sinuate; not folded, flat, and not bullate between the veins, glabrous and smooth both surfaces; adaxial matte and abaxial lustrous when young becoming slightly glaucous; flexible; variegated;

Leaf blade size: To about 30.5 cm long and about 19.1 cm wide about one-third way from the base; average about 28.5 cm long and 17.5 cm wide;

Leaf blade color: Early season and expanding adaxial margin nearest RHS 138A, center between RHS 145B and RHS 146D with intermediate zone comprising colors between RHS 138A and RHS 146D, between RHS 146D and RHS 145D and between RHS 145A and RHS 145B; abaxial season and expanding margin between RHS 146B and RHS 138A, center between RHS 146B and RHS 150D with intermediate zone comprising colors of nearest RHS 146D, between RHS N144A and RHS N144D and between RHS 147C and RHS 145C; mid-season and mature adaxial margin between RHS NN137A and RHS 139A, center between RHS 11C and RHS 11D and RHS N144D with intermediate zone comprising colors of between RHS N144A and RHS 144A, between RHS 146C and RHS 146B, RHS 146A and RHS 146D; abaxial mid-season and mature margin between RHS 137A and RHS NN137B, center nearest RHS 11D with intermediate zone comprising colors of between RHS 138D and RHS 145D, between RHS N138D and RHS 139D and RHS 146C;

Veins: 11 to 13 pairs with midrib; slightly impressed adaxial and costate and smooth abaxial;

Vein color: Young adaxial margin region nearest RHS 146D and center nearest RHS 145A, young abaxial RHS 146C and center nearest RHS 145C; mature adaxial margin between RHS 146C and RHS 146B and center nearest RHS 156B, mature abaxial margin nearest RHS 146D and center nearest RHS 150D;

Petiole: Glabrous and matte both adaxial and abaxial; moderately concavo-convex; stiff; to 30.0 cm long and 18.0 mm wide at base and about 5.0 mm deep, average about 25.0 cm long and 15.0 mm wide and 4.0 mm deep;

Petiole color: Adaxial margin nearest RHS 138A, center nearest RHS 150D with longitudinal streaks of nearest RHS 144A; abaxial margin nearest RHS 138A, midrib nearest RHS 4D and region surrounding midrib nearest RHS 150D;

Flower description:

Buds one to two days prior to opening: Clavate with acute apex and narrow tube and rounded base; about 45.0 mm long and 12.0 mm in diameter at the widest portion in the bulb, tube to about 18.0 mm long and to about 3.0 mm diameter at base, gradually tapering from bulb;

Bud color: Nearest RHS 85C with apical 3.0 mm nearest RHS 160C;

Flowers: Perfect; incomplete; campanulate; attitude outwardly to slightly downwardly; to 59.0 mm long to exserted pistil; corolla to 57.0 mm long and 26.0 mm wide at apex, fused in basal 35.0 mm, free in the distal 24.0 mm, decreasing in size distally; corolla tube portion 19.0 mm long and gradually tapering to 3.0 mm diameter at base; with rounded base; flowers tightly arranged on scape;

Flowering lasting: Persists for a normal period, usually about one day on plant;

Flowering period: Scapes remain effective with flowers beginning mid-June for about three to three and a half weeks; with about 38 flowers per scape; mostly secund;

Fragrance: No detectable fragrance;

Tepal: Two sets of three; clavate; entire margins; acute apex; fused in basal 35.0 mm; glabrous adaxial and abaxial; outer set to about 9.0 mm wide and 57.0 mm long; inner set to about 9.0 mm wide and 57.0 mm long;

Tepal color: Outer set adaxial nearest RHS 85D in 3.0 mm longitudinal center and nearest RHS NN155D along edges, abaxial lighter than RHS 85D along center and nearest RHS NN155D along edge; inner set adaxial nearest RHS 85D in 3.0 mm longitudinal center and nearest RHS NN155D along edges, abaxial lighter than RHS 85D along center and nearest RHS NN155D along edge, with a transparent 0.5 mm wide margin; corolla tube adaxial nearest RHS NN155C, abaxial between RHS NN155D and RHS 85D;

Gynoecium: Single; to about 59.0 mm long; superior;

*Style*.—Cylindrical; glabrous; to about 52.0 mm long and 0.7 mm diameter; straight with distal 9.0 mm arcuate upwards 90°; color lighter than RHS 145D proximally and nearest RHS 155C distally.

*Stigma*.—Puberulent; tri-lobed; about 1.0 mm long and 1.0 mm diameter; color nearest RHS NN155A.

*Ovary*.—Ellipsoidal; superior; apex rounded; base rounded to truncate; sides slightly furrowed, about 6.0 mm long and 2.5 mm diameter; color nearest RHS 145A.

Androecium: Six;

*Filaments*.—Six; cylindrical; approximately 55.0 mm long and 0.5 mm in diameter; curved or bent upwardly about 90° in the distal 8.0 mm; color in distal one-half nearest RHS 155D transitioning to nearest RHS 145D in the proximal one-third.

*Anthers*.—Oblong with rounded ends; basifixed, longitudinally dehiscent; about 5.0 mm long and 2.0 mm wide when fully developed; color nearest RHS 199B.

*Pollen*.—Abundant; spherical; less than 0.1 mm long; color nearest RHS 17A.

Peduncle: Cylindrical; usually one per mature division; about 3 per plant; glabrous; moderately glaucous; erect; to about 78.7 cm tall, and about 9.0 mm in diameter at base, average about 68.2 cm tall and 8.0 mm diameter at base;

Inflorescence: Flowering portion about 22.0 cm long and 7.0 cm wide; with variegated bracts with medium green margins and light yellowish-green centers subtending each flower;

Peduncle color: Proximal portion below leaves between RHS 145D and RHS 160D and distal portion between RHS 157C and RHS 158D with undertone of nearest RHS 138B and variable light blush of nearest RHS 183D;

Pedicel: Cylindrical; glabrous; slightly lustrous; to about 10.0 mm long and 2.0 mm diameter, decreasing distally; attitude outwardly to slightly arcuate outwardly;

Pedicel color: Between RHS 148D and RHS 146D with faint blush of nearest RHS N77B;

Floral bracts: Each flower normally subtended by a single variegated bract; lanceolate; narrowly acute apex and truncate base; entire margin; glabrous and slightly glaucous abaxial and adaxial; to about 42.0 mm long 12.0 mm wide, decreasing distally; variegated margin about 2 to 3 mm wide;

Bract color: At flowering adaxial and abaxial margin between RHS 138A and RHS 137, adaxial center nearest RHS 158D with undertone of nearest RHS 160C and a faint blush of nearest RHS N77B, abaxial center nearest RHS 155B with a faint variable blush of nearest RHS N7B;

Fruit: Non-fleshy, dehiscent, tri-loculicidal capsule; oblong ellipsoidal; rounded base; acute to apiculate apex; about 24.0 mm long and 5.0 mm in diameter; color as maturing nearest RHS 146D, when nearly mature and prior to dehiscence nearest RHS 150D and upon dehiscence nearest RHS 161C;

Seeds: Elliptic; with flattened wing surrounding embryo positioned toward one end of ellipse; about 8 mm long, 2.5 mm wide and 1.0 mm thick at embryo; typically 10 to 30 per capsule; color nearest RHS 202A with maturity;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'Love Story' as herein described and illustrated.

* * * * *